US011534420B2

(12) United States Patent
Hoffman

(10) Patent No.: US 11,534,420 B2
(45) Date of Patent: Dec. 27, 2022

(54) COMPOSITIONS AND METHODS FOR TREATING CANCER

(71) Applicant: Tyme, Inc., New York, NY (US)

(72) Inventor: Steven Hoffman, Mahwah, NJ (US)

(73) Assignee: TYME, INC., New York, NY (US)

( * ) Notice: Subject to any disclaimer, the term of this patent is extended or adjusted under 35 U.S.C. 154(b) by 0 days.

(21) Appl. No.: 16/874,092

(22) Filed: May 14, 2020

(65) Prior Publication Data

US 2020/0360328 A1    Nov. 19, 2020

Related U.S. Application Data

(60) Provisional application No. 62/847,570, filed on May 14, 2019.

(51) Int. Cl.
| | | |
|---|---|---|
| A61K 31/19 | (2006.01) | |
| A61K 38/34 | (2006.01) | |
| A61K 9/00 | (2006.01) | |
| A61P 35/00 | (2006.01) | |
| A61K 31/198 | (2006.01) | |
| A61K 31/4166 | (2006.01) | |
| A61K 31/407 | (2006.01) | |
| A61K 31/37 | (2006.01) | |
| A61K 31/436 | (2006.01) | |
| A61K 31/55 | (2006.01) | |

(52) U.S. Cl.
CPC .......... *A61K 31/198* (2013.01); *A61K 9/0053* (2013.01); *A61K 31/19* (2013.01); *A61K 31/37* (2013.01); *A61K 31/407* (2013.01); *A61K 31/4166* (2013.01); *A61K 31/436* (2013.01); *A61K 31/55* (2013.01); *A61K 38/34* (2013.01); *A61P 35/00* (2018.01)

(58) Field of Classification Search
CPC ...... A61K 31/19; A61K 31/198; A61K 31/37; A61K 31/407; A61K 31/4166; A61K 31/436; A61K 31/55; A61K 38/34; A61K 9/0053; A61K 9/00; A61P 35/00
See application file for complete search history.

(56) References Cited

U.S. PATENT DOCUMENTS

| | | |
|---|---|---|
| 4,029,547 A | 6/1977 | Umezawa et al. |
| 4,117,161 A | 9/1978 | Pozuelo |
| 4,165,382 A | 8/1979 | Pozuelo |
| 4,389,415 A | 6/1983 | Scriabine |
| 4,957,910 A | 9/1990 | Sutton et al. |
| 5,029,760 A | 7/1991 | Gamblin |
| 5,167,448 A | 12/1992 | Herold et al. |
| 5,206,018 A | 4/1993 | Sehgal et al. |
| 5,225,435 A | 7/1993 | Pawelek et al. |
| 5,292,933 A | 3/1994 | Harsanyi et al. |
| 5,310,539 A | 5/1994 | Williams |
| 5,733,926 A | 3/1998 | Gorbach |
| 5,853,753 A | 12/1998 | Maierhoffer et al. |
| 5,929,055 A | 7/1999 | Ryan et al. |
| 5,945,411 A | 8/1999 | Larson et al. |
| 5,952,374 A | 9/1999 | Clarkson, Jr. et al. |
| 6,359,001 B1 | 3/2002 | Drago |
| 8,268,352 B2 | 9/2012 | Vaya et al. |
| 8,481,498 B1 | 7/2013 | Hoffman |
| 9,549,969 B2 | 1/2017 | Hoffman |
| 9,585,841 B2 | 3/2017 | Hoffman |
| 9,687,528 B2 | 6/2017 | Hoffman |
| 9,724,657 B2 | 8/2017 | Hoffman |
| 9,895,425 B2 | 2/2018 | Hoffman |
| 10,010,590 B2 | 7/2018 | Hoffman |
| 10,272,068 B2 | 4/2019 | Hoffman |
| 10,307,465 B2 | 6/2019 | Hoffman |
| 10,507,198 B2 | 12/2019 | Hoffman |
| 10,646,552 B2 | 5/2020 | Hoffman |
| 10,905,698 B1 | 2/2021 | Hoffman et al. |
| 11,052,068 B2 | 7/2021 | Hoffman |
| 11,058,638 B2 | 7/2021 | Hoffman |
| 11,097,234 B2 | 8/2021 | Hoffman |
| 2002/0128304 A1 | 9/2002 | D'Amato |
| 2002/0132353 A1 | 9/2002 | Tamura et al. |
| 2007/0072800 A1 | 3/2007 | Gengrinovitch et al. |
| 2008/0113951 A1 | 5/2008 | El Nagger et al. |
| 2008/0193511 A1 | 8/2008 | Massing |
| 2009/0123571 A1 | 5/2009 | Meehan |
| 2010/0040642 A1 | 2/2010 | Schultz-Cherry et al. |
| 2010/0104660 A1 | 4/2010 | Yu |
| 2010/0239661 A1 | 9/2010 | Roy et al. |
| 2011/0104765 A1 | 5/2011 | Halloran et al. |
| 2011/0118528 A1 | 5/2011 | Longo et al. |
| 2013/0116215 A1 | 5/2013 | Coma et al. |

(Continued)

FOREIGN PATENT DOCUMENTS

| | | |
|---|---|---|
| CA | 2601794 A1 | 3/2006 |
| CA | 3069703 A1 | 1/2019 |

(Continued)

OTHER PUBLICATIONS

Zhang et al., "In vivo activation of the human CYP3A4 promoter in mouse liver and regulation by pregnane X receptors," Biochemical Pharmacology, 2003, 65: 1889-1896. (Year: 2003).*

Aoki et al., "Bastadin 6, a spongean brominated tyrosine derivative, inhibits tumor angiogenesis by inducing selective apoptosis to endothelial cells," Anti-Cancer Drugs, 2006, 17: 269-278. (Year: 2006).*

International Search Report and Written Opinion issued in PCT/US2020/032847, dated Jul. 22, 2020.

Böni, et al., "Radioiodine-labelled alpha-methyl-tyrosine in malignant melanoma: cell culture studies and results in patients", British Journal of Dermatology, Jul. 1997, vol. 137, Issue 1, pp. 96-100.

(Continued)

*Primary Examiner* — Julie Ha

(74) *Attorney, Agent, or Firm* — Morgan, Lewis & Bockius, LLP

(57) ABSTRACT

Disclosed are methods for treating cancer by reduction of glycogen stores and administering tyrosine derivatives.

18 Claims, No Drawings

(56) References Cited

U.S. PATENT DOCUMENTS

| | | |
|---|---|---|
| 2013/0183263 A1 | 7/2013 | Hoffman |
| 2013/0243873 A1 | 9/2013 | Aversa et al. |
| 2014/0128460 A1 | 5/2014 | Hegde |
| 2014/0350284 A1 | 11/2014 | Halloran et al. |
| 2014/0369942 A1 | 12/2014 | Lee et al. |
| 2015/0072967 A1 | 3/2015 | Rodrigues et al. |
| 2015/0111878 A1 | 4/2015 | Hoffman |
| 2015/0216827 A1 | 8/2015 | Hoffman |
| 2016/0199453 A1 | 7/2016 | Hoffman |
| 2017/0029892 A1 | 2/2017 | Lombard |
| 2017/0080093 A1 | 3/2017 | Hoffman |
| 2017/0137532 A1 | 5/2017 | Liu |
| 2017/0266206 A1 | 9/2017 | Li et al. |
| 2017/0319698 A1 | 11/2017 | Vergnault et al. |
| 2017/0333451 A1 | 11/2017 | Hoffman |
| 2018/0071316 A1 | 3/2018 | Hoffman |
| 2018/0185374 A1 | 7/2018 | Moorman et al. |
| 2018/0193360 A1 | 7/2018 | Hoffman |
| 2019/0091252 A1 | 3/2019 | Hoffman |
| 2019/0201378 A1 | 7/2019 | Hoffman |
| 2019/0298677 A1 | 10/2019 | Hoffman |
| 2020/0215082 A1 | 7/2020 | Hoffman |
| 2020/0254067 A1 | 8/2020 | Hoffman |
| 2020/0345753 A1 | 11/2020 | Hoffman |
| 2020/0360328 A1 | 11/2020 | Hoffman |
| 2020/0405680 A1 | 12/2020 | Hoffman |
| 2021/0106549 A1 | 4/2021 | Hoffman |
| 2021/0169903 A1 | 6/2021 | Hoffman et al. |
| 2021/0220312 A1 | 7/2021 | Hoffman |
| 2021/0275467 A1 | 9/2021 | Hoffman et al. |
| 2021/0353645 A1 | 11/2021 | Hoffman et al. |
| 2021/0379014 A1 | 12/2021 | Hoffman |
| 2021/0386832 A1 | 12/2021 | Hoffman |
| 2022/0002227 A1 | 1/2022 | Zucaro |

FOREIGN PATENT DOCUMENTS

| | | | |
|---|---|---|---|
| CN | 102397550 A | 5/2013 | |
| CN | 103919787 A | 7/2014 | |
| CN | 106031731 A | 10/2016 | |
| CN | 110563602 A | 12/2019 | |
| DE | 4342174 C1 | 5/1995 | |
| DE | 19906977 C1 | 6/2000 | |
| EP | 1281324 A2 | 2/2003 | |
| EP | 1961418 A1 | 8/2008 | |
| EP | 2208497 A1 | 7/2010 | |
| EP | 3020392 A1 | 5/2016 | |
| EP | 3488848 A1 | 5/2019 | |
| EP | 2978419 B1 | 4/2020 | |
| JP | H03161442 A | 7/1991 | |
| JP | 2001-521540 A | 11/2001 | |
| JP | 2004 300143 A | 10/2004 | |
| JP | 2015-509101 A | 3/2015 | |
| JP | 2016-534071 A | 11/2016 | |
| WO | WO 1991/00270 A1 | 1/1991 | |
| WO | WO 98/47515 A1 | 10/1998 | |
| WO | WO 2002/066019 A2 | 8/2002 | |
| WO | WO 2002/098403 A1 | 12/2002 | |
| WO | WO 2005/072061 A2 | 8/2005 | |
| WO | WO 2005/072706 A2 | 8/2005 | |
| WO | WO 2006/099685 A1 | 9/2006 | |
| WO | WO 2007/016766 A1 | 2/2007 | |
| WO | WO 2007/120153 A1 | 10/2007 | |
| WO | WO 2007/128442 A1 | 11/2007 | |
| WO | WO 2011/053835 A1 | 5/2011 | |
| WO | WO 2011/093559 A1 | 8/2011 | |
| WO | WO 2011/129765 A1 | 10/2011 | |
| WO | WO 2012/123819 A1 | 9/2012 | |
| WO | WO 2012/165984 A1 | 12/2012 | |
| WO | WO 2013/096870 A1 | 6/2013 | |
| WO | WO 2013/109610 A1 | 7/2013 | |
| WO | WO-2013109610 A1 * | 7/2013 | ............. A61P 35/00 |
| WO | WO 2014/045023 A1 | 3/2014 | |
| WO | WO 2014/078724 A1 | 5/2014 | |
| WO | WO 2014/158547 A1 | 10/2014 | |
| WO | WO 2015/061256 A1 | 4/2015 | |
| WO | WO 2015/061288 A1 | 4/2015 | |
| WO | WO 2015/061328 A2 | 4/2015 | |
| WO | WO 2016/105530 A1 | 6/2016 | |
| WO | WO 2016/167944 A2 | 10/2016 | |
| WO | WO 2017/117158 A1 | 7/2017 | |
| WO | WO 2017/160895 A1 | 9/2017 | |
| WO | WO-2017160895 A1 * | 9/2017 | ........... A61K 9/0014 |
| WO | WO 2017/201217 A1 | 11/2017 | |
| WO | WO 2018/049141 A1 | 3/2018 | |
| WO | WO 2018/093820 A1 | 5/2018 | |
| WO | WO 2018/102506 A1 | 6/2018 | |
| WO | WO 2018/195411 A1 | 10/2018 | |
| WO | WO 2018/204669 A1 | 11/2018 | |
| WO | WO 2019/018633 A1 | 1/2019 | |
| WO | WO 2019/055747 A1 | 3/2019 | |
| WO | WO 2019/130637 A1 | 7/2019 | |
| WO | WO 2020/018292 A1 | 1/2020 | |
| WO | WO 2020/023191 A1 | 1/2020 | |
| WO | WO 2020/112766 A1 | 6/2020 | |
| WO | WO 2020/160398 A1 | 8/2020 | |
| WO | WO 2020/181100 A1 | 10/2020 | |
| WO | WO 2020/197875 A1 | 10/2020 | |
| WO | WO 2020/214879 A1 | 10/2020 | |
| WO | WO 2020/232227 A1 | 11/2020 | |
| WO | WO 2021/015437 A1 | 1/2021 | |
| WO | WO 2021/076723 A1 | 4/2021 | |
| WO | WO 2021/119096 A1 | 6/2021 | |
| WO | WO 2021/146506 A2 | 7/2021 | |
| WO | WO 2021/207487 A1 | 10/2021 | |
| WO | WO 2021/231931 A1 | 11/2021 | |
| WO | WO 2021/231934 A1 | 11/2021 | |
| WO | WO 2021/231936 A1 | 11/2021 | |
| WO | WO 2022/006366 A1 | 1/2022 | |

OTHER PUBLICATIONS

Brogden, et al., "α-Methyl-p-tyrosine: A review of its Pharmacology and Clinical Use", Drugs, Feb. 1981, vol. 21, No. 2, pp. 81-89.

Bubeck, et al., "Melanoma affine radiopharmaceuticals—A comparative study of 131l-labeled quinoline and tyrosine derivatives," European Journal of Nuclear Medicine, No. 6, 1981, pp. 227-233.

Del Priore, et al., "SM88 in non-metastatic rising PSA-recurrent prostate cancer", Journal of Clinical Oncology, 2017, 35, 2017 ASCO Annual Meeting, Suppl.; abstract e16567, 2 pages.

Ell, "Brain Tumor Uptake of iodo-alpha-methyl-tyrosine", Journal of Nuclear Medicine, Nov. 1991, vol. 32, No. 11, pp. 2193-2193.

Hoffman, et al., "An open-label trial of SMK treatment of advanced metastatic cancer", 18th World Congress on Controversies in Obstetrics, Gynecology Infertility (COGI), Oct. 24-27, 2013, 8 pages.

Hoffman, et al., "SM88/SMK non-hormonal therapy in recurrent or untreated prostate cancer", Journal of Clinical Oncology, 2017, 35, 2017 ASCO Annual Meeting, Suppl.; abstract e16540, 1 page.

Hoffman, et al., "SMK/SM88 toxicity, efficacy, and patient reported outcomes in metastatic pancreas cancer", Journal of Clinical Oncology, 2017, 35, 2017 ASCO Annual Meeting, Suppl.; abstract e14060, 1 page.

Nakagami, et al., "A Case of Malignant Pheochromocytoma Treated with $^{131}$I-metaiodobenzylguanidine and Alpha-Methyl-p-Tyrosine", Japanese Journal of Medicine, May-Jun. 1990, vol. 29, No. 3, pp. 329-333.

Okada, et al., "A Long Survived Case of Malignant Pheochromocytoma Treated With Alpha-Methyl-P-Tyrosine and Midaglizol (DG-5128)", Journal of Japan Society for Cancer; Jan. 1990; one page (Abstract Only).

Ram, et al., "Failure of alpha-methyltyrosine to prevent hypertensive crisis in pheochromocytoma", Archives of Internal Medicine, Nov. 1985, vol. 145, No. 11, pp. 2114-2115.

Sokol, et al., "1605P—Preclinical animal data of the S1\488 tyrosine isomer," European Society for Medical Oncology (ESMO) 2016 Congress, Oct. 2016, Poster.

Steinsapir, et al., "Metyrosine and pheochromocytoma", Archives of Internal Medicine, Apr. 1997, vol. 157, No. 8, pp. 901-906.

Tada, et al., "Three Cases of Malignant Pheochromocytoma Treated with Cyclophosphamide, Vincristine, and Dacarbazine Combina-

(56) References Cited

OTHER PUBLICATIONS tion Chemotherapy and Alpha-Methyl-p-Tyrosine to Control Hypercatecholaminemia", Hormone Research, Jan. 1998, vol. 49, No. 6, pp. 295-297.
Voorhess, "Effect of alpha-methyl-p-tyrosine on 3,4-dihydroxyphenylalanine (DOPA) excretion of hamsters with melanotic melanoma", Cancer Research, Mar. 1968, vol. 28, pp. 452-454.
Zimmermann, et al., "Prolonged Inhibition of Presynaptic Catecholamine Synthesis With α-Methyl-Para-Tyrosine Attenuates the Circadian Rhythm of Human TSH Secretion," J. Soc. Gynecol Investing, May/Jun. 2001, vol. 8, No. 3, pp. 174-178.
U.S. Appl. No. 17/440,415, filed Sep. 17, 2021, Zucaro.
Banerjee, et al., "Pharmacokinetic and biodisturbution study of eserine and pralidoxime chloride in rabbits following a single application of a transdermal patch," Eur J Drug Metab Pharmacokinet, vol. 41, No. 3, Dec. 30, 2014.
Bloemen, et al: Challenge and Therapeutic Studies Using Alpha-Methyl-Para-Tyosine (AMPT) in Neuropsychiatric Disorders A Review Central Nervous System Agents in Medicinal Chemistry, vol. 8, No. 4, pp. 249-256, Dec. 1, 2008.
Cho, et al., "Minimum effective drug concentrations of a transdermal patch system containing procyclidine and physostigmine for prohylaxis against soman poisoning in rhesus monkeys" Environmental Toxicology And Pharmacology, vol. 33, No. 1, pp. 1-8, Oct. 7, 2011.
Cohen, et al., "Anisomycin, a Protein Synthesis Inhibitor, Disrupts Traumatic Memory Consolidation and Attenuates Posttraumatic Stress Response in Rats," Biological Psychiatry, Elsevier Science, vol. 60, No. 7, pp. 767-776, Oct. 1, 2006.
Cools, "Athetoid and Choreiform Hyperkinesias Produced by Caudate Application of Dopmine In Cats," Psychopharmacologia (Berl.) vol. 25, pp. 229-237, 1972.
Daniel, F., et al., "A Pilot Study of Stanozolol for Advanced Breast Carcinoma Cancer," Stanozolol For Advanced Breast CA, vol. 67, No. 12, pp. 2966-2968, Jun. 15, 1991.
Davidson, et al., "Management of Generalized Anxiety Disorder in Primary Care: Identifying the Challenges and Unmet Needs," Prim Care Companion J Clin Psychiatry 2010;12(2): e1-e13.
Elia, et al. "Tauroursodeoxycholic acid in tHe treatment of patients with amyotrophic lateralsclerosis", European Journal of Neurology, vol. 23, No. 1, pp. 45-52, Feb. 9, 2015.
Fernandez-Zapico, et al., "Abstract B15: Therapeutic potential of targeting amino acid metabolism in pancreatic cancer," Cancer Res vol. 79 (24_Supplement): B15, Dec. 13, 2019.
Fillit, et al., "Observations in a preliminary open trial of estradiol therapy for senile dementi-alzheimer's type" Psychoneuroendocrinologyvol. 11, No. 3, pp. 337-345, 1986.
Gartrell, et al., "Phase II trial of SM-88, a cancer metabolism based therapy, in non-metastatic biochemical recurrent prostate cancer," Investigational New Drugs, vol. 39, No. 2, pp. 499-508, Sep. 13, 2020.
George, et al., "Altered locus coeruleus-norepinephrine function following single prolonged stress," European Journal of Neuroscience, vol. 37, No. 6, pp. 901-909, Dec. 20, 2012.
Hayat, et al: "A Randomized Comparison of Maintenance Treatment with Androgens, Immunotherapy, and Chemotherapy in Adult Acute Myelogenous Leukemia, A Leukemia-Lymphoma Group Trial of the EORTC," Cancer, vol. 58, pp. 617-623, 1986.
International Search Report & Written Opinion, PCT Application No. PCT/US2013/021714, dated Jul. 25, 2013, 10 pages.
International Search Report & Written Opinion, PCT Application No. PCT/US2014/061527, dated Jan. 29, 2015, 9 pages.
International Search Report & Written Opinion, PCT Application No. PCT/US2014/061481, dated Feb. 5, 2015, 2015, 10 pages.
International Search Report & Written Opinion, PCT Application No. PCT/US2014/061590, dated Jun. 1, 2015, 8 pages.
International Search Report & Written Opinion, PCT Application No. PCT/US2016/024432, dated Mar. 5, 2017, 11 pages.
International Search Report & Written Opinion, PCT Application No. PCT/US2016/068774, dated Mar. 15, 2017, 11 pages.
International Search Report & Written Opinion, PCT Application No. PCT/US2017/022386, dated May 17, 2017, 11 pages.
International Search Report & Written Opinion, PCT Application No. PCT/US2017/033213, dated Jul. 7, 2017, 10 pages.
International Search Report & Written Opinion, PCT Application No. PCT/US2017/050653, dated Jan. 1, 2018, 21 pages.
International Search Report & Written Opinion, PCT Application No. PCT/US2017/061682, dated Feb. 1, 2018, 8 pages.
International Search Report & Written Opinion, PCT Application No. PCT/US2017/063865, dated Feb. 26, 2018, 11 pages.
International Search Report & Written Opinion, PCT Application No. PCT/US2018/028552 dated Jul. 9, 2018, 8 pages.
International Search Report & Written Opinion, PCT Application No. PCT/US2018/042874, dated Oct. 9, 2018, 11 pages.
International Search Report & Written Opinion, PCT Application No. PCT/US2018/051010, dated Jan. 1, 2019, 9 pages.
International Search Report & Written Opinion, Applicatioin No. PCT/US2019/040581, dated Aug. 16, 2019, 6 pages.
International Search Report & Written Opinion, PCT Application No. PCT/US2019/040264, dated Nov. 13, 2019, 10 pages.
International Search Report & Written Opinion, PCT Application No. PCT/US2019/063242, dated Nov. 3, 2020, 10 pages.
International Search Report & Written Opinion, PCT Application No. PCT/US2020/023299, dated Jun. 19, 2020, 10 pages.
International Search Report & Written Opinion, PCT Application No. PCT/US2020/016086, dated Apr. 23, 2020, 8 pages.
International Search Report & Written Opinion, PCT Application No. PCT/US2020/021212, dated Jun. 23, 2020, 9 pages.
International Search Report & Written Opinion, PCT Application No. PCT/US2020/028624, dated Jul. 14, 2020, 7 pages.
International Search Report & Written Opinion, PCT Application No. PCT/US2020/032847, dated Jul. 22, 2020, 2020, 7 pages.
International Search Report & Written Opinion, PCT Application No. PCT/US2020/055727, dated Feb. 1, 2021, 10 pages.
International Search Report & Written Opinion, PCT Application No. PCT/US2020/063962, dated Mar. 2, 2021, 10 pages.
International Search Report & Written Opinion, PCT Application No. PCT/US2021/013555, dated Jul. 14, 2021, 25 pages.
International Search Report & Written Opinion, PCT Application No. PCT/US2021/026370, dated Jul. 7, 2021, 8 pages.
International Search Report & Written Opinion, PCT Application No. PCT/US2021/032557, dated Jul. 14, 2021, 25 pages.
International Search Report & Written Opinion, PCT Application No. PCT/US2021032566, dated Aug. 17, 2021, 10 pages.
International Search Report & Written Opinion, PCT Application No. PCT/US2021032562, dated Aug. 18, 2021, 7 pages.
International Search Report & Written Opinion, PCT Application No. PCT/US2021/040035, dated Oct. 12, 2021, 7 pages.
Jockusch, et al., Triphosphates of the Two Components in DESCOVY and TRUVADA are Inhibitors of the SARS-CoV-2 Polymerase, BioRxiv,Apr. 5, 2020 (Apr. 5, 2020) pp. 1-8.
Kewalramani, A et al: "Asthma and Mood Disorders". Int J Child Health Hum Dev. 2008; 1 (2): 115-123.
Kliachina, et al., "Design, synthesis and biological evaluation of novel tetrahydroacridine pyridine-aldoxime and amidoxime hybrids as efficient uncharged reactivators of nerve agent-inhibited human acetylcholinesterase", European Journal Of Medicinal Chemistry, vol. 78, pp. 455-467, Mar. 15, 2014.
Kundu, et al: "Cross-Talk between Bile Acids and Gastrointestinal Tract for Progression and Development of Cancer and Its Therapeutic Implications." IUBMB Life, Voll. 67, No. 7, 2015, pp. 514-523.
Liu, et al., "Structure Activity Relationships of Small Phosphopeptides, Inhibitors of Grb2 SH2 Domain, and Their Prodrugs," Journal of Medicinal Chemistry, vol. 47, No. 5, pp. 1223-1233, Feb. 1, 2004.
Longhurst, et al. "Effects of catecholamine depletion with AMPT (alpha-methyl-para-tyrosine) in obessive-complusive disorder," Biological Psychiatry, Elsevier Science, New York, NY US, vol. 46, No. 4, dated Aug. 15, 1999, pp. 573-576.
Macedo, "Role of Androgens on MCF-7 Breast Cancer Cell Growth and on the Inhibitory Effect of Letrozole", Cancer Research, vol. 66, No. 15, pp. 7775-7782, Aug. 1, 2006.

(56) References Cited

OTHER PUBLICATIONS

Obrecht, et al., "Novel open-chain and cyclic conformationally constrained (R)- and (S)-α, α-disubstituted tyrosine analogs", Helvetica Chimica ACTA, vol. 78, pp. 1567-1587, 1995.

Okada, et al., "A Long-Survived Case of Malignant Pheochromocytoma Treated with Alpha-Methyl-P-Tyrosine and Midaglizol (DG-5128)," Nihon Gan Chiryo Gakkai Shi., vol. 25, No. 6, pp. 1221-1225, Jun. 20, 1990.

Pasca, et al. "Using iPS cell-derived neurons to uncover cellular phenotypes associated with Timothy syndrome," Nature Medicine, vol. 17, No. 12, pp. 1657-1662, Dec. 7, 2011.

Russo, "Correlation Between Hepatocyte Growth Factor (HGF) and Gamma-Aminobutyric Acid (GABA) Plasma Levels in Autistic Children", Biomarker Insights, vol. 8, pp. 69-75, Jun. 1, 2013.

Schuppert, et al., "Therapy of a malignant sympathetic paraganlioma of the organ of Zuckerkandl—A case report," Klin Wochenschr (1991) 69:937-942.

Sokol, et al: "Preclinical animal data of the SM88 tyrosine isomer", Annals of Oncology, vol. 27, Suppl. 6, Oct. 2016.

Stega, et al., "A first-in-human study of the novel metabolism-bsed anti-cancer agent SM-99 in subjects with advanced metastatic cancer", Investigational New Drugs, vol. 38, No. 2, pp. 392-401, Mar. 30, 2019.

Szekely, et al., "NSAID use and dementia risk in the Cardiovascular Health Study*: Role of APOE and NSAID type", Neurology, vol. 70, No. 1, pp. 17-24, Nov. 14, 2007.

Tomsik, et al., "L-rhamnose and L-fucose suppress cancer growth in mice", Central European Journal of Biology, vol. 6, No. 1, pp. 1-9, Aug. 31, 2010.

Xing, et al: "Lidocaine Induces Apoptosis and Suppresses Tumor Growth in Human Hepatocellular Carcinoma Cells In Vitro and in a Xenograft Model In Vivo." Anesthesiology, vol. 126, No. 5, 2017, pp. 868-881.

* cited by examiner

COMPOSITIONS AND METHODS FOR TREATING CANCER

CROSS-REFERENCE TO RELATED APPLICATION

This application claims the benefit of U.S. Provisional Patent Application No. 62/847,570, filed May 14, 2019, the entirety of which is incorporated by reference herein.

TECHNICAL FIELD

The present invention provides methods for treating cancer.

BACKGROUND

Cancer cell metabolism differs markedly from that of normal cells. For example, cancer cells exhibit increased glucose metabolism and alterations in mitochondrial oxidative metabolism.

There is a need for additional methods of exploiting the metabolism of cancer cells to enhance treatment of the disease.

SUMMARY

The present disclosure provides methods of treating cancer by increasing the oxidative stress on the cancer cell.

In particular, the present disclosure is directed to methods of treating cancer in a subject comprising reducing the subject's glycogen stores; and administering to the subject an effective amount of a tyrosine derivative.

The present disclosure is further directed to methods of treating cancer in a subject comprising determining that the subject has been adhering to a diet that effects reduced glycogen stores, and administering to the subject a cancer therapy that comprises an effective amount of a tyrosine derivative.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment incudes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder. This condition, disease or disorder can be cancer.

The methods of the present disclosure comprise administering to a subject in need thereof an effective amount of a tyrosine derivative or a pharmaceutically acceptable salt thereof. As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with respect to the particular compound, component or composition selected, the route of administration, and the ability of the components to elicit a desired result in the individual, but also with respect to factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide improved therapeutic response. An effective amount is also one in which any toxic or detrimental effects of the components are outweighed by the therapeutically beneficial effects.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "stereoisomers" refers to compounds that have identical chemical constitution, but differ as regards the arrangement of the atoms or groups in space. The term "enantiomers" refers to stereoisomers that are mirror images of each other that are non-superimposable.

The term "administering" means either directly administering a compound or composition of the present invention, or administering a prodrug, derivative or analog which will form an equivalent amount of the active compound or substance within the body. The terms "subject," "individual," and "patient" are used interchangeably herein, and refer an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

The term "promoter" as used herein includes compounds that promote the expression or activity of a protein, polypeptide or enzyme and does not necessarily mean complete promotion of expression and/or activity. Rather, the promotion includes promotion of the expression and/or activity of a protein, polypeptide or enzyme to an extent, and for a time, sufficient to produce the desired effect.

In some aspects, the present disclosure is directed to methods of treating cancer in a subject comprising reducing the subject's glycogen stores; and administering to the subject an effective amount of a tyrosine derivative.

Glycogen is a glucose polymer that is stored in various tissues, in particular in the liver and the skeletal muscles. The term "glycogen stores," as used herein, refers to glycogen stored within cells. In some aspects, a patient's glycogen stores can be measured by measuring the glycogen stores in the patient's liver tissue. In other aspects, a patient's glycogen stores can be measured by measuring the glycogen stores in the patient's muscle tissue.

Glycogen stores in a subject's tissues can be measured by methods known in the art. See, e.g., Zios and Harris, Glycogen metabolism has a key role in the cancer microenvironment and provides new targets for cancer therapy, J Mol Med (2016) 94:137-154 at 145 (Methods for assessing glycogen stores).

The methods of the present disclosure comprise reducing the subject's glycogen stores. In this aspect of the disclosure, "reducing" (or "reduction") refers to quantitatively decreasing the amount of glycogen stored in the patient's cells relative to a baseline state. The baseline state is the glycogen level in the patient's cells at the initiation of performance of methods of the disclosure. In some embodiments of the methods of the disclosure, reduction of the glycogen stores in the patient's cells may be demonstrated by showing a reduction in the glycogen stores in the patient's liver tissue. In other embodiments of the methods of the disclosure, reduction of the glycogen stores in the patient's cells may be demonstrated by showing a reduction in the glycogen stores in the patient's muscle tissue.

In the methods of the present disclosure, the glycogen stores can be reduced using any methods known to effect a reduction of glycogen. Examples of methods know to effect reduction of glycogen stores include adherence to a ketogenic diet, adherence to a low carbohydrate diet, adherence to a calorie-restricted diet, and adherence to a period of fasting.

In some embodiments, reduction of the subject's glycogen stores is effected through the subject's adherence to a ketogenic diet. As used herein, a "ketogenic diet" refers to a diet consisting of a weight ratio ranging from 3:1 to 4:1 of fat to protein plus carbohydrate. This weight ratio translates to a caloric composition of about 90% from fat, about 8% from protein, and about 2% from carbohydrates.

In other embodiments, reduction of the subject's glycogen stores is effected through the subject's adherence to a low carbohydrate diet. The United States Department of Agriculture recommends a diet having a caloric composition of 45-65% from carbohydrate, 20-35% from fat, and 10-15% from protein. As used herein, the term "low carbohydrate diet" refers to any diet in which less than 45% of the calories come from carbohydrates. Thus, in some embodiments, the low-carbohydrate diet is a diet in which less than 45% of the calories come from carbohydrates.

In some embodiments, the low carbohydrate diet is a diet in which less than 40% of the calories come from carbohydrates. In other embodiments, the low carbohydrate diet is a diet in which less than 35% of the calories come from carbohydrates. In other embodiments, the low carbohydrate diet is a diet in which less than 30% of the calories come from carbohydrates. In other embodiments, the low carbohydrate diet is a diet in which less than 25% of the calories come from carbohydrates. In other embodiments, the low carbohydrate diet is a diet in which less than 20% of the calories come from carbohydrates. In other embodiments, the low carbohydrate diet is a diet in which less than 15% of the calories come from carbohydrates. In other embodiments, the low carbohydrate diet is a diet in which less than 10% of the calories come from carbohydrates. In other embodiments, the low carbohydrate diet is a diet in which less than 5% of the calories come from carbohydrates.

An example of a low carbohydrate diet, the Atkins Diet®, consists of a caloric composition of about 64% from fat, 32% from protein, and 4% from carbohydrates.

In other embodiments, reduction of the subject's glycogen stores is effected through the subject's adherence to a calorie-restricted diet. As used herein, the term "calorie-restricted diet" refers to a diet in which the subject's daily caloric intake is 1000 calories or less. Thus, in some embodiments, the calorie-restricted diet results in a daily caloric intake of 1000 calories of less.

In other embodiments, the calorie restricted diet results in a daily caloric intake of about 900 calories or less. In other embodiments, the calorie restricted diet results in a daily caloric intake of about 800 calories or less. In yet other embodiments, the calorie restricted diet results in a daily caloric intake of about 700 calories or less. In yet other embodiments, the calorie restricted diet results in a daily caloric intake of about 600 calories or less. In yet other embodiments, the calorie restricted diet results in a daily caloric intake of about 500 calories or less.

In some embodiments, reduction of the subject's glycogen stores is effected through the subject's adherence to a period of fasting for at least 8 hours. As used herein, the term "fasting" refers to abstaining from the intake of food having a caloric content, or drink having a caloric content. In some embodiments, the period of fasting will last at least 8 hours. In other embodiments, the period of fasting lasts at least 10 hours. In yet other embodiments, the period of fasting lasts at least 12 hours. In yet other embodiments, the period of fasting lasts at least 15 hours. In yet other embodiments, the period of fasting lasts at least 18 hours. In yet other embodiments, the period of fasting lasts at least 20 hours. In yet other embodiments, the period of fasting lasts at least 22 hours. In yet other embodiments, the period of fasting lasts at least 24 hours.

In some embodiments, the subject's glycogen stores are reduced by at least 10%. In other embodiments, the subject's glycogen stores are reduced by at least 20%. In other embodiments, the subject's glycogen stores are reduced by at least 30%. In other embodiments, the subject's glycogen stores are reduced by at least 40%. In other embodiments, the subject's glycogen stores are reduced by at least 50%. In other embodiments, the subject's glycogen stores are reduced by at least 60%. In other embodiments, the subject's glycogen stores are reduced by at least 70%. In other embodiments, the subject's glycogen stores are reduced by at least 80%. In other embodiments, the subject's glycogen stores are reduced by at least 90%. In yet other embodiments, the subject's glycogen stores are reduced by more than 90%.

In some aspects, the subject's glycogen stores are reduced concurrently with administering to the subject an effective amount of a tyrosine derivative.

In other aspects, the reduction of the subject's glycogen stores is effected for a period of time prior to administration of the tyrosine derivative. In some embodiments, the reduction is effected for a period of at least 8 hours prior to the administration of the tyrosine derivative. In other embodiments, the reduction is effected for a period of at least 24 hours prior to the administration of the tyrosine derivative. For example, the reduction can be effected for a period of 8, 9, 10, 11, 12, 13, 14, 15, 16, 17, 18, 19, 20, 21, 22, 23, or 24 hours prior to the administration of the tyrosine derivative. In other embodiments, the reduction is effected for a period of at least one week prior to the administration of the tyrosine derivative. In other embodiments, the reduction is effected for a period of at least two weeks prior to the administration of the tyrosine derivative. In other embodiments, the reduction is effected for a period of at least three weeks prior to the administration of the tyrosine derivative.

In some aspects, the present disclosure is directed to a method of treating cancer in a subject comprising determining that the subject has been adhering to a diet that effects reduced glycogen stores, and administering to the subject a cancer therapy that comprises an effective amount of a tyrosine derivative. In some embodiments, the diet that effects reduced glycogen stores is a ketogenic diet, a low carbohydrate diet, a calorie-restricted diet, or a period of fasting, as described previously. In some embodiments, determining whether the subject has been adhering to a diet that effects reduced glycogen stores comprises reviewing a diet diary kept by the subject. In some embodiments, determining whether the subject has been adhering to a diet that effects reduced glycogen stores comprises administering an instrument that asks the subject what he or she has ingested over a specified period of time. In yet other embodiments, determining whether the subject has been adhering to a diet that effects reduced glycogen stores comprises assessing the glycogen level within the subject's cells as described previously, and comparing that level to the glycogen level in the subject's cells determined at an earlier point in time.

Administration of the tyrosine derivative according to the methods of the present disclosure can be through various routes, including orally, nasally subcutaneously, intravenously, intramuscularly, transdermally, vaginally, rectally or in any combination thereof.

In certain embodiments, tyrosine derivative can be capable of existing in different isomeric forms, including stereoisomers and enantiomers. The tyrosine derivative can, for example, exist in both L-form or D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy]phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy]benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine methyl ester hydrochloride, H-3,5-diiodo-tyrosine methyl ester hydrochloride, H-D-3,5-diiodo-tyrosine methyl ester hydrochloride, H-D-tyrosine methyl ester hydrochloride, D-tyrosine methyl ester hydrochloride, D-tyrosine-methyl ester hydrochloride, methyl D-tyrosinate hydrochloride, H-D-tyrosine methyl ester•hydrochloride, D-tyrosine methyl ester hydrochloride, H-D-tyrosine methyl ester-hydrochloride, (2R)-2-amino-3-(4-hydroxyphenyl) propionic acid, (2R)-2-amino-3-(4-hydroxyphenyl) ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,542)-OSu, Fmoc-tyrosine(3-NO2)-OH, α-methyl-L-tyrosine, α-methyl-D-tyrosine, α-methyl-DL-tyrosine, and $C_1$-$C_{12}$ alkylester salts of α-methyl-DL-tyrosine such as α-methyl-DL-tyrosine methyl ester hydrochloride. In certain embodiments of the invention, the tyrosine derivative is α-methyl-L-tyrosine. In other embodiments, the tyrosine derivative is α-methyl-D-tyrosine. In other embodiments, the tyrosine derivative is α-methyl-DL-tyrosine in a racemic form.

The tyrosine derivative can be administered during a cycle consisting of five to seven days of administering the tyrosine derivative, and one to two days of not administering the tyrosine derivative. The tyrosine derivative can be administered over the course of at least six said cycles. In one suitable embodiment of the invention, the tyrosine derivative is administered daily. In another suitable embodiment of the invention, the tyrosine derivative is administered multiple times per day. In some embodiments, the tyrosine derivative is administered three times per day.

In some aspects, about 10-2000 mg of the tyrosine derivative (e.g., α-methyl-DL-tyrosine) is administered daily, preferably, 100-1200 mg of the tyrosine derivative is administered daily, most preferably, 300-900 mg of the tyrosine derivative (e.g., α-methyl-DL-tyrosine) is administered daily. The tyrosine derivative (e.g., α-methyl-DL-tyrosine) is preferably administered orally. The daily dosages can be administered as a single dose or in substantially equal, divided doses throughout the day. Three, substantially equal daily doses of the tyrosine derivative (e.g., α-methyl-DL-tyrosine) are particularly preferred.

In some embodiments, tyrosine derivative is administered in substantially equal, divided doses.

Preferred aspects of the disclosure are directed to methods of treating cancer in a patient by administering an effective amount of α-methyl-DL-tyrosine to the patient.

In some embodiments of the present methods, the tyrosine derivative is administered to the patient in combination with other medications. As used herein, administering drugs in combination does not imply any particular dosing regimen, but rather means that both drugs are present in or on the patient's body at the same time. Thus, drugs administered in combination may be administered simultaneously, or may be administered sequentially (e.g., at different times during the day).

In some embodiments, the tyrosine derivative is administered in combination with a Cytochrome p450 3A4 promoter. "Cytochrome p450 3A4" (which can be abbreviated as "CPY 3A4") is a member of the cytochrome p450 superfamily of enzymes, and is a mixed-function oxidase that is involved in the metabolism of xenobiotics in the body. Representative CPY 3A4 promoters are 5,5-diphenylhydantoin (sold commercially as, for example, Dilantin), valproic acid, and carbamazepine, which are believed to induce expression of the CPY 3A4 enzyme. In some embodiments, the CPY 3A4 promoter is 5,5-diphenylhydantoin, valproic acid, or carbamazepine.

Thus, in some embodiments, the present disclosure provides methods of treating cancer comprising administering to a subject in need thereof an effective amount of a tyrosine derivative and a CPY 3A4 promoter. In some embodiments, the tyrosine derivative is α-methyl-DL-tyrosine and the CPY 3A4 promoter is 5,5-diphenylhydantoin, valproic acid, or carbamazepine.

In other embodiments, the tyrosine derivative is administered in combination with melanin, methoxsalen, melanotan II, or a combination thereof. Thus, in some embodiments, the present disclosure provides methods of treating cancer comprising administering to a subject in need thereof an effective amount of a tyrosine derivative and melanin, methoxsalen, melanotan II, or a combination thereof. In some embodiments, α-methyl-DL-tyrosine is administered in combination with melanin, methoxsalen, melanotan II, or a combination thereof.

In other embodiments, the present disclosure provides methods of treating cancer comprising administering to a subject in need thereof an effective amount of a tyrosine derivative, a CPY 3A4 promoter, and melanin, methoxsalen, melanotan II, or a combination thereof. Thus, in some embodiments, α-methyl-DL-tyrosine is administered in combination with 5,5-diphenylhydantoin, valproic acid, or carbamazepine, and with melanin, methoxsalen, melanotan II, or a combination thereof.

In other embodiments, the tyrosine derivative is administered in combination with a compound that inhibits the PI3K/mTor signaling pathway. Activation of the PI3K/mTOR pathway results in control of cell growth and survival in a manner that provides cancer cells with growth advantage, metastatic competence, angiogenesis, and drug resistance. Examples of compounds that deactivate the PI3K/mTor signaling include leucine aminopeptidase inhibitors (alternatively known as leucyl aminopeptidase inhibitors), rapamycin, temsirolimus (CCI-779), everolimus (RAD001), and ridaforolimus (AP-23573).

In some embodiments, the compound that inhibits the PI3K/mTor signaling pathway is a leucine aminopeptidase inhibitor. Leucine aminopeptidases are enzymes that preferentially catalyze the hydrolysis of leucine residues at the N-terminus of peptides and/or proteins. Representative leucine aminopeptidase inhibitors are N-[(2S,3R)-3-amino-2-hydroxy-4-phenylbutyryl]-L-leucine, and rapamycin.

Thus, in some embodiments, α-methyl-DL-tyrosine is administered in combination with a compound that inhibits the PI3K/mTor signaling pathway.

In other embodiments, methyl-DL-tyrosine is administered in combination with leucine aminopeptidase inhibitors, rapamycin, temsirolimus, everolimus, or ridaforolimus.

In some embodiments, α-methyl-DL-tyrosine is administered in combination with N-[(2S,3R)-3-amino-2-hydroxy-4-phenylbutyryl]-L-leucine or rapamycin. In some embodiments, α-methyl-DL-tyrosine is administered in combination with N-[(2S,3R)-3-amino-2-hydroxy-4-phenylbutyryl]-L-leucine. In other embodiments, α-methyl-DL-tyrosine is administered in combination with rapamycin.

In some embodiments, the present disclosure provides methods of treating cancer comprising administering to a subject in need thereof an effective amount of a tyrosine derivative, a CPY 3A4 promoter, melanin, methoxsalen, melanotan II, or a combination thereof; and a compound that inhibits the PI3K/mTor signaling pathway.

Thus, in some embodiments, the present disclosure provides methods of treating cancer comprising administering to a subject in need thereof an effective amount of a tyrosine derivative, a CPY 3A4 promoter, melanin, methoxsalen, melanotan II, or a combination thereof; and N-[(2S,3R)-3-amino-2-hydroxy-4-phenylbutyryl]-L-leucine or rapamycin.

In some embodiments, the present disclosure provides methods of treating cancer comprising administering to a subject in need thereof an effective amount of α-methyl-DL-tyrosine; 5,5-diphenylhydantoin, valproic acid, or carbamazepine; melanin, methoxsalen, melanotan II, or a combination thereof; and N-[(2S,3R)-3-amino-2-hydroxy-4-phenylbutyryl]-L-leucine or rapamycin.

In some embodiments, the methods of the disclosure optionally include administering a growth hormone inhibitor. Growth hormone (such as, for example, pancreatic growth hormone) induces cell replication. Representative growth hormone inhibitors are octreotide, somatostatin, and seglitide.

In some embodiments, the methods of the disclosure optionally include administering D-leucine. D-leucine is a stereoisomer of the naturally occurring L-leucine, the form of leucine incorporated into polypeptides and proteins. D-leucine cannot be incorporated into polypeptides and/or proteins. Along with the leucine aminopeptidase inhibitor, the D-leucine is believed to create a physiological environment that mimics a leucine shortage. Thus, the presence of D-leucine permits the use of lower doses of leucine aminopeptidase inhibitor in a pharmaceutical composition.

In some embodiments, the methods include simultaneous or at least contemporaneous administration of at least two of: (1) the tyrosine derivative, (2) melanin or a melanin promoter, (3) CPY 3A4 promoter, and (4) a compound that inhibits the PI3K/mTor signaling pathway. In other embodiments, the methods include simultaneous or at least contemporaneous administration of at least two of: (1) the tyrosine derivative, (2) melanin or a melanin promoter, (3) CPY 3A4 promoter, and (4) leucine aminopeptidase inhibitor. In other embodiments, the methods include simultaneous or at least contemporaneous administration of at least three of: (1) the tyrosine derivative, (2) melanin or a melanin promoter, (3) CPY 3A4 promoter, and (4) leucine aminopeptidase inhibitor. In other embodiments, the methods include simultaneous or at least contemporaneous administration of each of: (1) the tyrosine derivative, (2) melanin or a melanin promoter, (3) CPY 3A4 promoter, and (4) leucine aminopeptidase inhibitor.

The desired number of inhibitors and promoters can be provided in a single dosage form or any number of desired dosage forms, including in individual dosage forms. Representative dosage forms include tablets, capsules, caplets, sterile aqueous or organic solutions, reconstitutable powders, elixirs, liquids, colloidal or other types of suspensions, emulsions, beads, beadlets, granules, microparticles, nanoparticles, and combinations thereof. The amount of composition administered will, of course, be dependent on the subject being treated, the subject's weight, the severity of the condition being treated, the manner of administration, and the judgment of the prescribing physician.

Administration of the melanin, promoters, and/or inhibitors can be through various routes, including orally, nasally, subcutaneously, intravenously, intramuscularly, transdermally, vaginally, rectally or in any combination thereof. Transdermal administration can be effected using, for example, oleic acid, 1-methyl-2-pyrrolidone, or dodecylnonaoxyethylene glycol monoether.

The melanin, promoters and/or inhibitors can be administered during a cycle consisting of five to seven days of administering the melanin, promoters and/or inhibitors and one to two days of not administering the melanin, promoters and/or inhibitors. The melanin, promoters and/or inhibitors can be administered over the course of at least six of said cycles. It can be desirable to administer these components about two hours between meals to facilitate uptake.

In certain embodiments of the present invention, a pharmaceutical composition or combination therapy may be administered to a human patient for 5 days per week for a period of 6 weeks, creating one cycle of 30 days of treatment. Depending on the outcome after 6 weeks or one cycle of treatment, additional cycles of the pharmaceutical composition or combination therapy may be administered.

In some embodiments, the subject is administered a daily dose of 230 mg of α-methyl-DL tyrosine, 0.5 mg rapamycin, 50 mg phenytoin, and 10 mg methoxsalen.

In some embodiments, the subject is administered a daily dose of 300 mg of α-methyl-DL tyrosine, 0.5 mg rapamycin, 50 mg phenytoin, and 10 mg methoxsalen.

In some embodiments of the methods, 60 mg of the tyrosine derivative is administered orally and 0.25 mL of a 2 mg/mL suspension of the tyrosine derivative is administered subcutaneously.

In other embodiments, 10 mg of the methoxsalen is administered orally and 0.25 mL of a 1 mg/mL suspension of the methoxsalen is administered subcutaneously.

In other embodiments, 30 mg of the 5,5-diphenylhydantoin is administered orally. The CPY 3A4 promoter can also be valproic acid or carbamazepine.

In yet other embodiments, 20 mg of the N-[(2S,3R)-3-amino-2-hydroxy-4-phenylbutyryl]-L-leucine is administered orally. In other embodiments, 0.5 mg of rapamycin is administered. In one representative method, 60 mg of the tyrosine derivative is administered orally and 0.25 mL of a 2 mg/mL suspension of the tyrosine derivative is administered subcutaneously; 10 mg of the methoxsalen is administered orally and 0.25 mL of a 1 mg/mL suspension of the methoxsalen is administered subcutaneously; 30 mg of the 5,5-diphenylhydantoin is administered orally; and 20 mg of the N-[(2S,3R)-3-amino-2-hydroxy-4-phenylbutyryl]-leucine is administered orally.

In certain embodiments, the combination therapy comprises: (i) a dosage form containing melanin (50 mcg) and α-methyl-DL-tyrosine (75 mg); (ii) a dosage form containing 5,5-diphenylhydantoin (15 mg) and α-methyl-DL-tyrosine (75 mg); (iii) a dosage form containing 3-amino-2-hydroxy-4-phenylbutyryl]-L-leucine (50 mcg) and α-methyl-DL-tyrosine (75 mg); (iv) a dosage form containing 3-amino-2-hydroxy-4-phenylbutyryl]-L-leucine (5 mcg), melanotan II (10 mcg), and 5,5-diphenylhydantoin (2 mg); and (v) a dosage form containing α-methyl-DL-tyrosine (5 mg) in NaCl bacteriostatic water. In other embodiments, the combination therapy comprises: (i) a dosage form containing melanin (50 mcg) and α-methyl-DL-tyrosine (75 mg); (ii) a dosage form containing 5,5-diphenylhydantoin (15 mg) and α-methyl-DL-tyrosine (75 mg); (iii) a dosage form containing rapamycin (0.2 mg) and α-methyl-DL-tyrosine (75 mg); (iv) a dosage form containing rapamycin (0.15 mcg), melanotan II (10 mcg), and 5,5-diphenylhydantoin (2 mg); and (v) a dosage form containing α-methyl-DL-tyrosine (5 mg) in NaCl bacteriostatic water. Dosages that are two times greater than this, and even four times greater than this, are believed to be both safe and efficacious.

The present methods can include not only the steps of reducing the patients glycogen stores or determining that the subject has been adhering to a diet that effects reduced glycogen stores, and the administration step, but also the step of assessing progression of said cancer in said subject and/or the extent of cellular proliferation. The assessing step can be performed before or after the administering step.

Methods of reducing cell proliferation in a subject are also provided comprising reducing the subject's glycogen stores or determining that the subject has been adhering to a diet that effects reduced glycogen stores and administering an effective amount of a tyrosine derivative, to the subject in need thereof. In some embodiments, the methods further comprise administering one or more of melanin and/or a melanin promoter; a CPY 3A4 promoter; and a compound that inhibits the PI3k/mTor signaling pathway, to the subject in need thereof. In some embodiments, the methods further comprise administering one or more of melanin and/or a melanin promoter; a CPY 3A4 promoter; and a leucine aminopeptidase inhibitor, to the subject in need thereof.

In some aspects, the methods of the disclosure are used to treat cancer. In some embodiments, the cancer is a metastatic cancer, non-small cell lung cancer such as stage IV non-small cell lung cancer, ovarian cancer, breast cancer, cervical cancer, pancreatic cancer, stomach cancer, brain cancer such as glioblastoma or glioma, liver cancer, testicular cancer, leukemia, lymphoma, non-Hodgkin lymphoma, appendix cancer, biliary cancer, choleangiocarcinoma, colon cancer, colorectal cancer, germ cell tumor, glioma, Hodgkin's lymphoma, lung cancer, neuroblastoma, prostate cancer, renal cancer, sarcoma, thyroid cancer, tongue cancer, Ewing sarcoma, soft-tissue sarcoma, head and neck cancer, tonsil squamous cell carcinoma, squamous cell throat cancer, gall bladder cancer, thyroid cancer, or urothelial cancer.

In some embodiments, the cancer is a metastatic cancer. In some embodiments, the cancer is non-small cell lung cancer such as stage IV non-small cell lung cancer. In some embodiments, the cancer is ovarian cancer. In some embodiments, the cancer is breast cancer. In some embodiments, the cancer is cervical cancer. In some embodiments, the cancer is pancreatic cancer. In some embodiments, the cancer is stomach cancer. In some embodiments, the cancer is brain cancer such as glioblastoma. In some embodiments, the cancer is liver cancer. In some embodiments, the cancer is testicular cancer. In some embodiments, the cancer is leukemia. In some embodiments, the cancer is lymphoma. In some embodiments, the cancer is appendix cancer. In some embodiments, the cancer is biliary cancer. In some embodiments, the cancer is choleangiocarcinoma. In some embodiments, the cancer is colon cancer. In some embodiments, the cancer is colorectal cancer. In some embodiments, the cancer is germ cell tumor. In some embodiments, the cancer is glioma. In some embodiments, the cancer is Hodgkin's lymphoma. In some embodiments, the cancer is lung cancer. In some embodiments, the cancer is neuroblastoma. In some embodiments, the cancer is prostate cancer. In some embodiments, the cancer is renal cancer. In some embodiments, the cancer is sarcoma. In some embodiments, the cancer is thyroid cancer. In some embodiments, the cancer is tongue cancer. In some embodiments, the cancer is tonsil squamous cell carcinoma. In some embodiments, the cancer is urothelial cancer.

In other embodiments, the cancer is adenoid cystic carcinoma, adrenal gland cancer, amyloidosis, anal cancer, ataxia-telangiectasia, atypical mole syndrome, basal cell carcinoma, bile duct cancer, birt Hogg Dube syndrome, bladder cancer, bone cancer, breast cancer in men, carcinoid tumor, ductal carcinoma, endometrial cancer, esophageal cancer, gastric cancer, gastrontestinal stromal tumor—GIST, HER2-positive breast cancer, islet cell tumor, juvenile polyposis syndrome, kidney cancer, laryngeal cancer, leukemia—acute lymphoblastic leukemia, leukemia—acute lymphocytic (ALL), leukemia—acute myeloid AML, leukemia—adult, leukemia—childhood, leukemia—chronic lymphocytic—CLL, leukemia—chronic myeloid—CIVIL, lobular carcinoma, lung cancer—small cell, lymphoma—Hodgkin's, lymphoma—non-Hodgkin's, malignant glioma, melanoma, meningioma, multiple myeloma, myelodysplastic syndrome (MDS), nasopharyngeal cancer, neuroendocrine tumor, oral cancer, osteosarcoma, pancreatic neuroendocrine tumors, parathyroid cancer, penile cancer, peritoneal cancer, Peutz-Jeghers syndrome, pituitary gland tumor, polycythemia vera, renal cell carcinoma, retinoblastoma, salivary gland cancer, sarcoma, sarcoma—Kaposi, skin cancer, small intestine cancer, thymoma, uterine (endometrial) cancer, vaginal cancer, or Wilms' tumor.

In some embodiments, the methods of the disclosure further comprise radiotherapy to the subject.

Also provided herein are kits comprising a tyrosine derivative together with packaging for same which are useful in performing the methods of the present disclosure. The tyrosine derivative can include tyrosine derivatives capable of existing in isomeric form. The tyrosine derivatives can include tyrosine derivatives in its L-form or in its D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy]benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine-methyl ester hydrochloride, H-3,5-diiodo-tyrosine-methyl ester hydrochloride, H-D-3,5-diiodo-tyrosine-methyl ester hydrochloride, H-D-tyrosine-methyl ester hydrochloride, D-tyrosine methyl ester hydrochloride, D-tyrosine-ome hydrochloride, methyl D-tyrosinate hydrochloride, H-D-tyrosine-methyl ester•hydrochloride, D-tyrosine methyl ester hydrochloride, H-D-tyrosine-methyl ester-hydrochloride, (2R)-2-amino-3-(4-hydroxyphenyl) propionic acid, (2R)-2-amino-3-(4-hydroxyphenyl)methyl ester hydrochloride, methyl (2R)-2-amino-3-(4-hydroxyphenyl) propanoate hydrochloride methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-I2)-OSu, Fmoc-tyrosine(3-NO2)-OH, α-methyl-L-tyrosine, α-methyl-D-tyrosine, α-methyl-DL-tyrosine, and $C_1$-$C_{12}$ alkylester salts of α-methyl-DL-tyrosine such as α-methyl-DL-tyrosine methyl ester hydrochloride. In certain embodiments of the invention, the tyrosine derivative is α-methyl-L-tyrosine. In other specific embodiments of the invention, the tyrosine derivative is α-methyl-D-tyrosine. In other embodiments, the tyrosine derivative is α-methyl-DL-tyrosine in a racemic form.

Also provided herein are kits including a combination therapy with packaging for same which are useful in performing the methods of the present disclosure. Representative kits comprise a tyrosine derivative, melanin and/or a melanin promoter, a CPY 3A4 promoter, a compound that inhibits the PI3K/mTor signaling pathway (e.g., a leucine aminopeptidase inhibitor) and, optionally, a growth hormone inhibitor of the type described above, together with packaging for same. The kit can include one or more separate containers, dividers or compartments and, optionally, informational material such as instructions for administration. For example, each inhibitor or promoter (or the various combinations thereof) can be contained in a bottle, vial, or syringe, and the informational material can be contained in a plastic sleeve or packet or provided in a label. In some embodiments, the kit includes a plurality (e.g., a pack) of individual containers, each containing one or more unit dosage forms of a compound described herein. For example, the kit can include a plurality of syringes, ampules, foil packets, or blister packs, each containing a single unit dose of a compound described herein or any of the various combinations thereof. The containers of the kits can be air tight, waterproof (e.g., impermeable to changes in moisture or evaporation), and/or light-tight. The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

EXAMPLE 1 KETOGENIC DIET (3:1 RATIO BY WEIGHT OF FATS TO PROTEIN+CARBOHYDRATE FOR 8 HR)

A tumor sample taken from a human subject diagnosed with pancreatic cancer is analyzed for glycogen content. The subject ingests a ketogenic diet consisting of a 3:1 ratio by weight of fats to protein+carbohydrate for 8 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject continues to ingest only the ketogenic diet. At the end of 6 weeks, the tumor has decreased in size relative to a control population which received the same chemotherapy but did not ingest a ketogenic diet.

EXAMPLE 2 KETOGENIC DIET (4:1 RATIO BY WEIGHT OF FATS TO PROTEIN+CARBOHYDRATE FOR 24 HR)

A tumor sample taken from a human subject diagnosed with breast cancer is analyzed for glycogen content. The subject ingests a ketogenic diet consisting of a 4:1 ratio by weight of fats to protein+carbohydrate for 24 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject continues to ingest only the ketogenic diet. At the end of 6 weeks, the tumor has decreased in size relative to a control population which received the same chemotherapy but did not ingest a ketogenic diet.

EXAMPLE 3 KETOGENIC DIET (3:1 RATIO BY WEIGHT OF FATS TO PROTEIN+CARBOHYDRATE FOR ONE WEEK)

A tumor sample taken from a human subject diagnosed with colon cancer is analyzed for glycogen content. The subject ingests a ketogenic diet consisting of a 3:1 ratio by weight of fats to protein+carbohydrate for one week, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject continues to ingest only the ketogenic diet. At the end of 6 weeks, the tumor has decreased in size relative to a control population which received the same chemotherapy but did not ingest a ketogenic diet.

EXAMPLE 4 LOW CARBOHYDRATE DIET (LESS THAN 45% OF CALORIES FROM CARBOHYDRATES)

A tumor sample taken from a human subject diagnosed with pancreatic cancer is analyzed for glycogen content. The subject ingests a low carbohydrate diet in which less than 45% of the calories come from carbohydrates for 8 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject continues to ingest only the low carbohydrate diet. At the end of 6 weeks, the tumor has decreased in size relative to a control population which received the same chemotherapy but did not ingest a low carbohydrate diet.

EXAMPLE 5 LOW CARBOHYDRATE DIET (LESS THAN 35% OF CALORIES FROM CARBOHYDRATES)

A tumor sample taken from a human subject diagnosed with pancreatic cancer is analyzed for glycogen content. The subject ingests a low carbohydrate diet in which less than 35% of the calories come from carbohydrates for 8 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject continues to ingest only the low carbohydrate diet. At the end of 6 weeks, the tumor has decreased in size relative to a control population which received the same chemotherapy but did not ingest a low carbohydrate diet.

EXAMPLE 6 LOW CARBOHYDRATE DIET (LESS THAN 25% OF CALORIES FROM CARBOHYDRATES)

A tumor sample taken from a human subject diagnosed with pancreatic cancer is analyzed for glycogen content. The subject ingests a low carbohydrate diet in which less than 25% of the calories come from carbohydrates for 8 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject continues to ingest only the low carbohydrate diet. At the end of 6 weeks, the tumor has decreased in size relative to a control population which received the same chemotherapy but did not ingest a low carbohydrate diet.

EXAMPLE 7 CALORIE RESTRICTED DIET (1000 CALORIES/DAY)

A tumor sample taken from a human subject diagnosed with pancreatic cancer is analyzed for glycogen content. The subject ingests a calorie-restricted diet in which the subject consumes 1000 calories or less over 24 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject continues to ingest only a calorie-restricted diet in which the subject consumes 1000 calories per day. At the end of 6 weeks, the tumor has decreased in size relative to a control population which received the same chemotherapy but did not ingest a calorie-restricted diet.

EXAMPLE 8 CALORIE RESTRICTED DIET (800 CALORIES/DAY)

A tumor sample taken from a human subject diagnosed with pancreatic cancer is analyzed for glycogen content. The subject ingests a calorie-restricted diet in which the subject consumes 800 calories or less over 24 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject continues to ingest only a calorie-restricted diet in which the subject consumes 800 calories per day. At the end of 6 weeks, the tumor has decreased in size relative to a control population which received the same chemotherapy but did not ingest a calorie-restricted diet.

EXAMPLE 9 CALORIE RESTRICTED DIET (500 CALORIES/DAY)

A tumor sample taken from a human subject diagnosed with pancreatic cancer is analyzed for glycogen content. The subject ingests a calorie-restricted diet in which the subject consumes 500 calories or less over 24 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject continues to ingest only a calorie-restricted diet in which the subject consumes 500 calories per day. At the end of 6 weeks, the tumor has decreased in size relative to a control population which received the same chemotherapy but did not ingest a calorie-restricted diet.

EXAMPLE 10 FASTING (8 HOURS)

A tumor sample taken from a human subject diagnosed with pancreatic cancer is analyzed for glycogen content. The subject fasts for 8 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject fasts for 8 hours prior to each daily dose. At the end of 6 weeks, the tumor has decreased in size relative to a control population which received the same chemotherapy but did not ingest a calorie-restricted diet.

EXAMPLE 11 FASTING (10 HOURS)

A tumor sample taken from a human subject diagnosed with pancreatic cancer is analyzed for glycogen content. The subject fasts for 10 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject fasts for 10 hours prior to each daily dose. At the end of 6 weeks, the tumor has decreased in size relative to a control population which received the same chemotherapy but did not fast prior to therapy.

EXAMPLE 12 FASTING (12 HOURS)

A tumor sample taken from a human subject diagnosed with pancreatic cancer is analyzed for glycogen content. The subject fasts for 12 hours, after which a second tumor sample is taken from the subject and analyzed for glycogen content. The second tumor sample has a lower glycogen content than the first tumor sample. The subject is then administered a daily dose of 230 mg of α-methyl-DL tyrosine, 0.5 mg rapamycin, 50 mg phenytoin, and 10 mg methoxsalen for a period of 6 weeks, during which the subject fasts for 12 hours prior to each daily dose At the end of 6 weeks, the tumor has decreased in size relative to a control population which received the same chemotherapy but did not fast prior to therapy.

What is claimed:
1. A method of treating cancer in a subject comprising:
reducing the subject's glycogen stores, effected by adherence to a diet prior to and during administration of a tyrosine derivative, wherein the diet is a ketogenic diet; and
administering to the subject an effective amount of the tyrosine derivative.
2. The method of claim 1, wherein said diet further comprises adherence to a period of fasting for at least 8 hours.
3. The method of claim 1, wherein said reduction for a period of time prior to administration of the tyrosine derivative is at least 8 hours.

4. The method of claim 1, wherein said reduction is effected for at least three weeks prior to and during the administration of the tyrosine derivative.

5. The method of claim 1, wherein the tyrosine derivative is methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy]phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy]benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine methyl ester hydrochloride, H-3,5-diiodo-tyrosine methyl ester hydrochloride, H-D-3,5-diiodo-tyrosine methyl ester hydrochloride, H-D-tyrosine methyl ester hydrochloride, D-tyrosine methyl ester hydrochloride, D-tyrosine-methyl ester hydrochloride, methyl D-tyrosinate hydrochloride, H-D-tyrosine methyl esterhydrochloride, D-tyrosine methyl ester hydrochloride, H-D-tyrosine methyl ester-hydrochloride, (2R)-2-amino-3-(4-hydroxyphenyl) propionic acid, (2R)-2-amino-3-(4-hydroxyphenyl)methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-12)-OSu, Fmoc-tyrosine(3-NO2)-0H, a-methyl-L-tyrosine, a-methyl-D-tyrosine, a-methyl-DL-tyrosine, $C_1$-$C_{12}$ alkylester salts of a-methyl-DL-tyrosine, such as or a-methyl-DL-tyrosine methyl ester hydrochloride.

6. The method of claim 5, wherein the tyrosine derivative is a-methyl-DL-tyrosine.

7. The method of claim 1, wherein the tyrosine derivative is administered orally.

8. The method of claim 1, wherein 100-1200 mg of the tyrosine derivative is administered daily.

9. The method of claim 8, wherein 300-900 mg of the tyrosine derivative is administered daily.

10. The method of claim 1 wherein the tyrosine derivative is administered in substantially equal, divided doses.

11. The method of claim 1, further comprising administering an effective amount of a CPY 3A4 promoter.

12. The method of claim 11, wherein the CPY 3A4 promoter is 5,5-diphenylhydantoin, valproic acid, or carbamazepine.

13. The method of claim 1, further comprising administering melanin, methoxsalen, melanotan II, or a combination thereof.

14. The method of claim 1, further comprising administering a compound that inhibits the P13K/mTor signaling pathway.

15. The method of claim 1, further comprising administering a leucine aminopeptidase inhibitor.

16. The method of claim 1, further comprising administering N-[(2S,3R)-3-amino-2-hydroxy-4-phenylbutyryl]-L-leucine or rapamycin.

17. The method of claim 1, further comprising administering radiotherapy to the subject.

18. The method of claim 1, wherein the cancer is a metastatic cancer, non-small cell lung cancer, stage IV non-small cell lung cancer, ovarian cancer, breast cancer, cervical cancer, pancreatic cancer, stomach cancer, brain cancer, glioblastoma, liver cancer, testicular cancer, leukemia, lymphoma, appendix cancer, biliary cancer, cholangiocarcinoma, colon cancer, colorectal cancer, germ cell tumor, glioma, Hodgkin's lymphoma, lung cancer, neuroblastoma, prostate cancer, renal cancer, sarcoma, thyroid cancer, tongue cancer, tonsil squamous cell carcinoma, or urothelial cancer.

* * * * *